United States Patent [19]

McSpadden

[11] Patent Number: 4,457,710
[45] Date of Patent: * Jul. 3, 1984

[54] DENTAL INSTRUMENT

[75] Inventor: John T. McSpadden, Johnson City, Tenn.

[73] Assignee: Inventive Technology International, Johnson City, Tenn.

[*] Notice: The portion of the term of this patent subsequent to Oct. 12, 1999 has been disclaimed.

[21] Appl. No.: 319,266

[22] Filed: Nov. 9, 1981

Related U.S. Application Data

[63] Continuation-in-part of Ser. No. 63,436, Aug. 3, 1979, Pat. No. 4,299,571, Ser. No. 263,406, May 14, 1981, Pat. No. 4,332,561, and Ser. No. 297,007, Aug. 27, 1981, Pat. No. 4,353,698, which is a continuation of Ser. No. 105,761, Dec. 29, 1979, abandoned, which is a continuation-in-part of Ser. No. 970,464, Dec. 18, 1978, abandoned.

[51] Int. Cl.³ .............................................. A61C 5/02
[52] U.S. Cl. ...................................... 433/81; 433/164
[58] Field of Search ......................... 433/81, 102, 164

[56] References Cited

U.S. PATENT DOCUMENTS

| 636,359 | 11/1899 | Schultz | 433/102 |
|---|---|---|---|
| 1,307,446 | 6/1919 | Kerr | 433/102 |
| 1,771,182 | 7/1930 | Lentulo | 433/164 |
| 4,190,958 | 3/1980 | Martin et al. | 433/102 |
| 4,231,738 | 11/1980 | Riitano et al. | 433/102 |
| 4,299,571 | 11/1981 | McSpadden | 433/102 |

FOREIGN PATENT DOCUMENTS

| 279144 | 10/1913 | Fed. Rep. of Germany | 433/102 |
|---|---|---|---|
| 464121 | 6/1926 | Fed. Rep. of Germany | 433/164 |
| 519086 | 2/1931 | Fed. Rep. of Germany | 433/164 |
| 775073 | 12/1934 | France | 433/164 |

*Primary Examiner*—John J. Wilson
*Attorney, Agent, or Firm*—Luedeka & Neely

[57] ABSTRACT

An instrument particularly adapted for thermomechanically condensing a thermoplastic material such as gutta percha in the root canal of a tooth through the rotative action of the instrument is disclosed. The instrument comprises an elongated member including a shank at one end and a working portion at its other end. The working portion is tapered along at least part of its length. The working portion includes at least two oppositely disposed, continuous helical flutes formed in at least a portion of the tapered length of the shank defining at least two oppositely disposed helical shoulders. The shoulders face away from the shank and make an angle with the longitudinal axis of the working portion of from about 90° to 80° and each of the continuous spiraled flutes make from about 1.0 to 3.5 spirals per millimeter along the longitudinal axis of the working portion of the instrument. Preferably, the tapered end of the working portion is provided with a generally cylindrical, smooth walled pilot having a generally blunt end projecting coaxially from the tapered end of the working portion.

7 Claims, 5 Drawing Figures

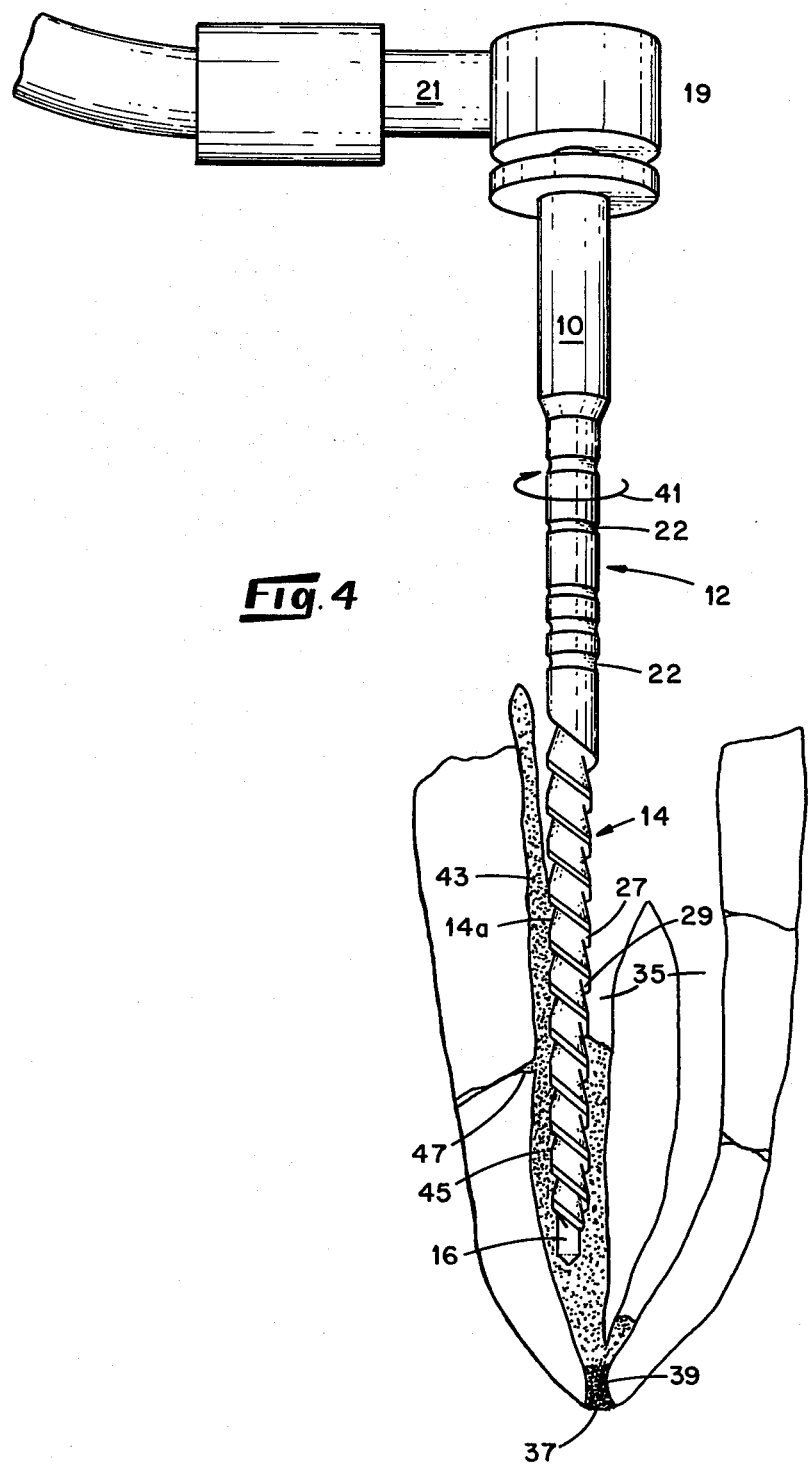

DENTAL INSTRUMENT

This application is a continuation-in-part of my prior application, Ser. No. 297,007, filed Aug. 27, 1981, now U.S. Pat. No. 4,353,698, Oct. 12, 1982, which is a continuation of my prior application Ser. No. 105,761, filed Dec. 29, 1979 (now abandoned), which is a continuation-in-part of my prior application Ser. No. 970,464, filed Dec. 18, 1978 (now abandoned); a continuation-in-part of my prior application Ser. No. 063,436, filed Aug. 3, 1979, now U.S. Pat. No. 4,299,571, Nov. 11, 1981; and a continuation-in-part of my prior application Ser. No. 263,406, filed May 14, 1981, now U.S. Pat. No. 4,332,561, June 1, 1982.

This invention relates to the field of dentistry and more specifically to the field of endodontics. In particular, the invention relates to a novel means and instrument for thermomechanically obturating extirpated root canals of teeth with gutta percha or other thermoplastic material.

In the field of dentistry, one of the most technically difficult mechanical operations is that of obturating (filling) an extirpated (stripped) root canal. The difficulty arises from the necessity of totally filling the root canal void in a homogeneous three-dimensional manner in order to prevent any leakage or communication between the root canal and the surrounding and supporting tissues of the tooth.

Various filler materials have been employed including filling paste and thermoplastic materials such as gutta percha. This invention relates to instrumentation for thermomechanically condensing gutta percha or similar thermoplastic material in an extirpated root canal. In the traditional technique for obturating a root canal with gutta percha, strand-like pieces of gutta percha, known as points, are inserted into the extirpated canal and then physically condensed by small tools known as "pluggers" and "spreaders". These tools are heated to soften the gutta percha points in the canal and then are hand manipulated to progressively feed and compact the points in the canal. The spreader is employed to move the gutta percha which has been softened by the heat of the instrument transversely of the canal, and the heated plugger is used to move the softened gutta percha longitudinally of the canal. Additional points are fed into the canal as the process proceeds in order to completely fill the root canal void.

One of the major difficulties involved in this procedure is that the canal must be filled three-dimensionally, filling any accessory or auxiliary canals and plugging and blocking as many openings as possible. In order to accomplish this, the dentist must have a high degree of skill and must expend a great deal of time in completing the process. The difficulty stems from the fact that each of the instruments used has essentially but one function, either moving the softened gutta percha generally transversely or generally longitudinally in the canal. Thus, in the case of an accessory canal the obturation of such canal depends upon using the proper tool at the proper time. Also, because of the manual nature of the operation, it is difficult to obtain a relatively uniform density of the condensed gutta percha in the canal.

I discovered that points of gutta percha or similar thermoplastic materials could be manipulated and condensed by a power-driven rotary instrument which operates on the principle of a reverse rotating screw. This technique employs the rotation effected by a dental hand piece which is of the low speed, high torque type to plasticize gutta percha by the thermomechanical action of the rotation of the instrument. The reverse screw effects distribution of the plasticized gutta percha in the root canal to effect its obturation. This technique greatly reduces the time required for obturation and is highly successful when employed by a skilled endodontist.

Work with the technique has shown that it is desirable to produce an instrument which can be operated at as low a rotational speed as possible to effect the plastization of the gutta percha and which will most effectively distribute the plasticized gutta percha in a balanced manner, both longitudinally and laterally of the extirpated canal.

Accordingly it is the principal object of this invention to provide an improved power-driven instrument of the class described.

Another object of the invention is to provide means for minimizing abrasive contact between the walls of the root canal and the instrument during use.

Other objects and advantages of the invention will become known by reference to the following description and accompanying drawings in which.

The illustrated embodiment shows an instrument particularly adapted for thermomechanically condensing a thermoplastic material such as gutta percha in the root canal of a tooth through the rotative action of the instrument. The instrument comprises an elongated member including a shank at one end and a working portion at its other end. The working portion is tapered along at least part of its length. The working portion includes at least two oppositely disposed, continuous helical flutes formed in at least a portion of the tapered length of the shank defining at least two oppositely disposed helical shoulders. The shoulders face away from the shank and make an angle with the longitudinal axis of the working portion of from about 90° to 80° and each of the continuous spiraled flutes make from about 1.0 to 3.5 spirals per millimeter along the longitudinal axis of the working portion of the instrument. Preferably, the tapered end of the working portion is provided with a generally cylindrical, smooth walled pilot having a generally blunt end projecting coaxially from the tapered end of the working portion.

Figure 1:
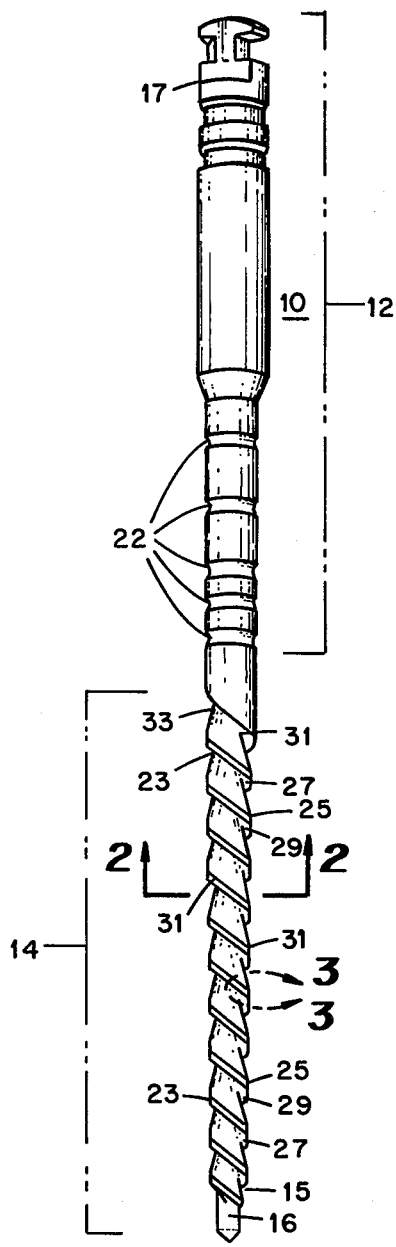
FIG. 1 is an elevational view of an embodiment of a dental instrument embodying various of the features of the invention.
Figure 2:
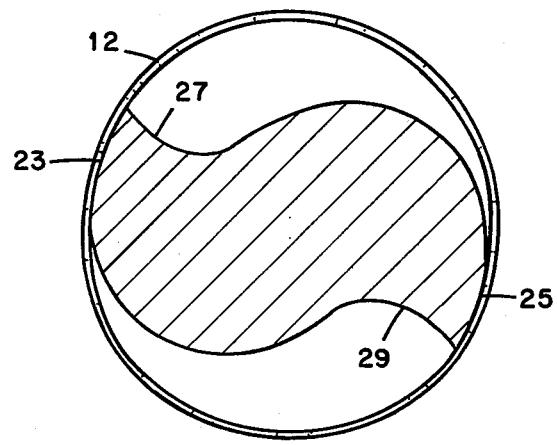
FIG. 2 is a sectional view taken along line 2—2 of FIG. 1.
Figure 3:
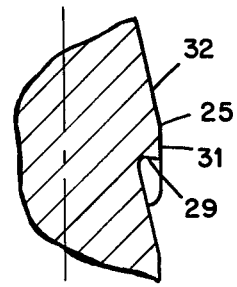
FIG. 3 is a sectional view taken along line 3—3 of FIG. 1.

Now with reference to the FIGS. 1, 2 and 3, the instrument, generally denoted by the numeral 10, has a shank 12 and a working portion 14. The working portion 14 is tapered along at least a portion of its length 13 to a tapered end 15 and a pilot 16 projects coaxially from the tapered end 15. The shank 12 above the working portion 14 is illustrated as being substantially cylindrical and is provided with a fitting 17 which is adapted to mate with the chuck 19 of a dental handpiece 21 (FIG. 4). The shank 12 is also preferably provided with indicia which can be aligned with the upper tooth structure to provide and indication of the depth of penetration of the instrument. As illustrated these indicia are in the form of spaced rings 22 formed in the shank.

Two continuous helical flutes 23 and 25 are formed in the tapered length of the shank 12 to provide two helical shoulders 27 and 29, respectively. The two continuous helical flutes are the first flute 23 and the second flute 25. The second flute 25 originates at a region, denoted as the numeral 31, 180° around the circumference of the working portion 14 from the origination region, denoted as the numeral 33, of the first flute 16. Each of these flutes 23 and 25 is a continuous flute from its point of origin to the tapered end 15 of the working portion 14.

The first continuous helical flute 23 defines a first continuous, helical shoulder 27 and the second continuous helical flute 25 defines a second continuous, helical shoulder 29. Each of these shoulders 27 and 29 is generally directed downwardly away from the shank and towards the tapered end 14 of the shank 12 as will be described below. As illustrated in FIG. 2, the shoulders 27 and 29 are slightly cupped which is the result of the grinding process employed in manufacturing the instrument, but they may be flat if another process is employed.

As illustrated, the flutes 23 and 25 follow a left-handed twist so that when rotated in a right-handed direction, the shoulders 27 and 29 force material outwardly from the centerline of the instrument and downwardly towards the tip of the instrument. However, it is contemplated that the flutes 23 and 25 can follow a right-handed twist if the direction of rotation is left handed.

In the preferred embodiment, minimization of possible abrasion is provided by the generally cylindrical pilot 16 which extends from the tapered end 15 of the working portion 14. The pilot 16 has a generally cylindrical, smooth wall and is integrally formed with and coaxially projects from the tapered end 15 of the working portion 14. The pilot 16 is formed with a distal end which is generally blunt and has no surfaces capable of abrading. Preferably, as illustrated the distal end is rounded so that the pilot 16 will not dig into or otherwise cut the tooth structure surrounding the root canal. It should be understood that other blunt shapes will also work. The pilot 16 is sized so that it will contact the wall of a curved root canal before the shoulders and associated lands adjacent the tip 15 of the instrument contact the wall of the root canal. Thus, the pilot 16 will tend to hold the the shoulders near the end of the working portion away from the wall of the root canal. The pilot also serves to stabilize the rotation of the instrument, since, as will be pointed out, it is immersed in plasticized gutta percha during operation so that it damps any vibrations or abberations caused by gutta percha of uneven density, contact with the walls of the cavity, etc. The diameter of the pilot 16 may be as large as the diameter of the tapered end 15 of the working portion 14. Preferably, the diameter of the pilot 16 is approximately of the order of the diameter of the working portion 14 near its end less the depth of the shoulders 27 and 29 so that the action of the shoulders 27 and 29 in advancing gutta percha is not materially interfered with. The length of the pilot may vary, but it has been determined that a length of about 0.5 to about 1.0 mm is satisfactory for substantially all applications to provide a minimization of abrasion and the desired damping or stabilizing action.

In order to further minimize abrasion with the walls of the root canal cavity, each of the flutes in the preferred embodiment is provided with a land 31. The presence of the land 31 provides a spiraled flat surface rather than a sharp edge which may contact the walls of the root canal cavity as the instrument is rotated. As illustrated in FIG. 3, the land 31 is at the periphery of the outer diameter of the shoulder 29 and provides a flat surface which will come in contact with the walls of the root canal if the instrument is moved laterally into contact with such walls. From the upper end of the land 31, the flute 26 tapers inwardly toward the inside diameter of the next adjacent shoulder, the surface indicated by 32. The land 31 on flute 23 is of similar configuration.

Figure 3A:
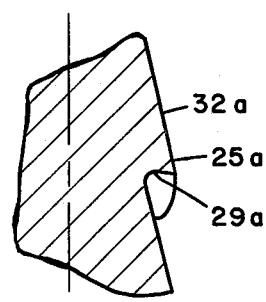
FIG. 3A is a view similar to FIG. 3 showing a modified shoulder construction; and, FIG. 4 is a fragmentary cross-sectional view of a tooth with the tool in a dental hand piece in working position in a root canal.

Satisfactory operation is also effected with flutes having a sharp edge as illustrated in FIG. 3A, wherein the flute 25a tapers inwardly toward the inside diameter of the next adjacent shoulder, the surface indicated by 32a, immediately from the outer diameter of the shoulder 29a.

The following is a description of use of the instrument and reference is made to FIG. 4. The root canal 35 is thoroughly cleaned and is shaped to provide adequate access in the usual manner. In order to prevent plasticized gutta percha from being forced through the apical foramen 37, a gutta percha point is selected which has a tip 39 slightly larger than the apical foramen. Sealer is applied to the tip 39 and it is inserted into the apical foramen 37 to seal it.

The instrument 10 which is sized to conform with the size of the cavity is coupled to the chuck 19 of a low speed, high torque hand piece 21 which is rotated in the direction of the arrow 41 at a speed of about 6,000 r.p.m. or less as determined by experience. A portion 14a of the working portion 14 of the instrument 10 is brought into contact with the surface of a gutta percha point 43 which has been placed in the canal. The rotation of the instrument causes the helical shoulders 27 and 29 to engage the gutta percha and to mechanically work it and to generate frictional heat which plasticizes the gutta percha which softens at a temperature of about 110°–112° F. under these conditions (with the direct application of heat without mechanical working the gutta percha does not soften until it reaches a temperature of from about 115°–120° F). The heat to soften the gutta percha is normally generated under the conditions outlined above in but a few seconds.

After the gutta percha has softened, the instrument is moved longitudinally in the canal to deliver the softened gutta percha into the pool 45 of gutta percha in the canal. The helix angle of the rotating shoulders 27 and 29 is such that the plasticized gutta percha is forced downwardly along the canal as well as laterally of the canal to uniformly fill the canal 35 and the auxiliary canals such as shown at 47. This process is repeated until the canal is completely obturated.

In order to obtain the necessary thermomechanical action on the unsoftened gutta percha point, the downwardly facing shoulders 27 and 29 should make an angle of not more than 90° with the axis of the instrument so that a cutting, chopping or shearing action occurs. If the angle of undercut is too great, e.g., less than about 70°, the lateral forces generated by the shoulder in the softened gutta percha are minimized thereby making the plugging of auxiliary canals and the like less certain. Preferably, the shoulders 27 and 29 make an angle of from about 90° to 80° to the axis of the instrument.

In operation, the double flutes and shoulders 27 and 29 provide a balanced torque on the instrument and a maximized shearing action which makes possible better plastization at a lower speed. The pilot 16 minimizes contact between the shoulders 27 and 29 at the tip 15 and the cavity wall and aids in negotiating corners. Also, the combination of the double fluted construction and the provision of the pilot 16 tends to stabilize the rotation of the instrument. The pilot 16 which is immersed in softened gutta percha damps lateral movements which may result from the interaction of the shoulders 27 and 29 with the gutta percha or the lands 31 with the walls of the cavity.

If the procedure outlined above is carried out with a single fluted instrument with a single spiraled shoulder as disclosed in several of my earlier applications, the rotation speed required to obtain satisfactory results in the absence of additional heat over and above that generated by the thermomechanical action of the instrument on the gutta percha is between about 8,000 and 13,000 r.p.m. Further, in the case of a single spiraled instrument, the balance between lateral and longitudinal movement of the plasticized gutta percha is heavily weighted towards longitudinal movement in the cavity as compared with the double fluted instrument.

The dimensions and parameters for a set of instruments as described above for the thermomechanical condensation of gutta percha or similar thermoplastic material are set forth in the attached table. The instruments are designed for operation at 6,000 r.p.m. or less and have shoulders 27 and 29 which are about 0.05–0.075 mm in depth, lands 31 which are about 0.05 mm in width. The pitch of the spiral for each of the flutes 23 and 25 which define the shoulder 27 and 29 can be determined by dividing the "Number of flutes/side/16 mm" given in the table by 2 (since there are two flutes which appear on each side) and then dividing that number into 16. Thus, if there are 18 flutes per side, each flute make nine spirals around the instrument and the pitch is 16 mm/9 spirals or 1.77 mm/spiral.

In general, flute spirals range of from about 1.0 mm/spiral to about 3.5 mm/spiral for each of the two flutes provides satisfactory operation with the smaller end of the range being employed with the smaller instruments.

TABLE

| Size | Nominal Diameter Across Shoulders at Tip mm | Pilot Diameter mm | Pilot Length mm | Working Portion Length mm | Number of Flutes /Side/ 16 mm |
|---|---|---|---|---|---|
| 25 | 0.25 | 0.15 | 0.635 | 16.0 | 24 ± 4 |
| 30 | 0.30 | 0.20 | 0.635 | 16.0 | 20 ± 4 |
| 35 | 0.35 | 0.25 | 0.635 | 16.0 | 20 ± 4 |
| 40 | 0.40 | 0.30 | 0.635 | 16.0 | 20 ± 4 |
| 45 | 0.45 | 0.35 | 0.635 | 16.0 | 18 ± 4 |
| 50 | 0.50 | 0.40 | 0.635 | 16.0 | 18 ± 4 |
| 60 | 0.60 | 0.50 | 0.635 | 16.0 | 15 ± 3 |
| 70 | 0.70 | 0.60 | 0.635 | 16.0 | 15 ± 3 |
| 80 | 0.80 | 0.70 | 0.635 | 16.0 | 15 ± 3 |
| 90 | 0.90 | 0.80 | 0.635 | 16.0 | 11 ± 2 |
| 100 | 1.00 | 0.90 | 0.635 | 16.0 | 11 ± 2 |
| 110 | 1.10 | 1.00 | 0.635 | 16.0 | 11 ± 2 |
| 120 | 1.20 | 1.10 | 0.635 | 16.0 | 11 ± 2 |
| 130 | 1.30 | 1.20 | 0.635 | 16.0 | 11 ± 2 |
| 140 | 1.40 | 1.30 | 0.635 | 16.0 | 11 ± 2 |

The use of the instruments described above provides a means to thermomechanically condense a thermoplastic material such as gutta percha in the root canal by mechanical means. Use has shown that the instrument, even in the smaller sizes has the required flexibility and resistance to fracture which makes possible its successful use with high torque hand pieces. Moreover, the instrument provides an excellent tactile sensation to the endodontist so that he can readily feel when the gutta percha point is plasticized when the side of the instrument is employed to plasticize the gutta percha, and can sense when the cavity is properly filled from reverse forces generated as the instrument is moved longitudinally to fill the canal.

The foregoing detailed description is given primarily for clearness of understanding, and no unnecessary limitations should be understood therefrom for modification will be obvious to those skilled in the art upon reading this disclosure and can be made without departing from the spirit of the invention or the scope of the appended claims.

What is claimed is:

1. An instrument for use with a dental hand piece for thermomechanically obturating a root canal with a thermoplastic material by a process wherein the thermoplastic material is softened by the mechanical working of the thermoplastic material effected by the rotative action of the instrument at a speed of less than about 6,000 r.p.m. and the softened thermoplastic material is distributed in the root canal by the rotational movement of the instrument, said instrument comprising an elongated member having a shank at one end thereof which includes a fitting for engagement with the chuck of a dental handpiece; a working portion at the other end of said member, the diameter of said working portion progressively decreasing away from said shank portion to provide a tapered working portion, flute means on said working portion defining a pair of opposed, continuous spiral flutes, each having a shoulder facing away from said shank and making an angle with the longitudinal axis of said working portion of from about 90° to about 80°, and each of said continuous spiraled flutes making from about 1.0 to about 3.5 spirals per millimeter along the longitudinal axis of said working portion.

2. The instrument of claim 1 wherein the tapered end of said working portion is provided with a smooth, generally cylinderical pilot which is coaxial with said working portion and which projects from the tapered end of said working portion, said pilot having a generally blunt end, said pilot having a diameter of approximately the diameter of the tapered end of said working portion and a length of from about 0.5–1.0 mm.

3. The instrument of claim 2 wherein said pilot has a diameter of from about the diameter of the tapered end of said working portion to about the diameter of said opposed shoulders.

4. The instrument of claim 2 wherein each of said continuous spiral flutes has a peripheral land adjacent the outside diameter of its associated shoulder before it tapers toward the inside diameter of an adjacent shoulder.

5. The instrument of claim 4 wherein the lands have a width of approximately 0.05 mm.

6. The instrument of claim 1 wherein each of said continuous spiral flutes has a peripheral land adjacent the outside diameter of its associated shoulder before it tapers toward the inside diameter of an adjacent shoulder.

7. The instrument of claim 6 wherein the lands have a width of approximately 0.05 mm.

* * * * *

UNITED STATES PATENT OFFICE
CERTIFICATE OF CORRECTION

Patent No. 4,457,710            Dated July 3, 1984

Inventor(s) John T. McSpadden

It is certified that error appears in the above-identified patent and that said Letters Patent are hereby corrected as shown below:

On the title page,
  Assignee: After "International" insert -- Inc. --

Signed and Sealed this

Ninth Day of April 1985

[SEAL]

Attest:

DONALD J. QUIGG

Attesting Officer      Acting Commissioner of Patents and Trademarks